United States Patent [19]

Diery et al.

[11] 4,339,459
[45] Jul. 13, 1982

[54] GUANIDINIUM COMPOUNDS AND THEIR USE AS MICROBIOCIDAL AGENTS

[75] Inventors: Helmut Diery, Kelkheim; Wolfgang Wagemann, Tremsbüttel; Hans-Walter Bücking, Kelkheim; Martin Hille, Liederbach; Karl H. Wallhäusser, Hofheim am Taunus, all of Fed. Rep. of Germany

[73] Assignee: Hoechst Aktiengesellschaft, Fed. Rep. of Germany

[21] Appl. No.: 216,164

[22] Filed: Dec. 15, 1980

[30] Foreign Application Priority Data

Dec. 21, 1979 [DE] Fed. Rep. of Germany ....... 2952167

[51] Int. Cl.³ .................. A61K 31/205; C07C 129/12
[52] U.S. Cl. ................................ 424/316; 424/326; 260/501.14; 564/236; 564/240
[58] Field of Search ............... 564/240, 236; 424/316, 424/326; 260/501.14

[56] References Cited

U.S. PATENT DOCUMENTS 4,092,432  5/1978  Bjorklund et al. .................. 564/236

FOREIGN PATENT DOCUMENTS 1156517  6/1969  United Kingdom ............... 564/236

Primary Examiner—Natalie Trousof
Assistant Examiner—L. Hendriksen
Attorney, Agent, or Firm—Connolly and Hutz

[57] ABSTRACT

Guanidiunium salts of the formula 1

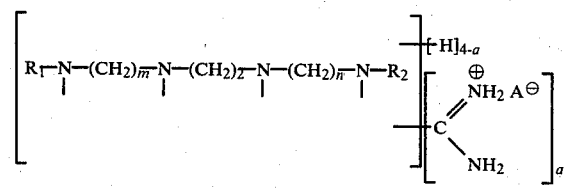

in which $R_1$ and $R_2$ are identical or different and denote alkyl, 2-hydroxyalkyl or alkenyl each having from 8 to 18 carbon atoms, or $C_8-C_{18}$ alkoxypropyl, m and n are 2 or 3, a is a number from 1 to 4 and A denotes an anion, process for their manufacture and their use as microbiocidal agents.

2 Claims, No Drawings

GUANIDINIUM COMPOUNDS AND THEIR USE AS MICROBIOCIDAL AGENTS

This invention relates to guanidinium salts of the formula 1

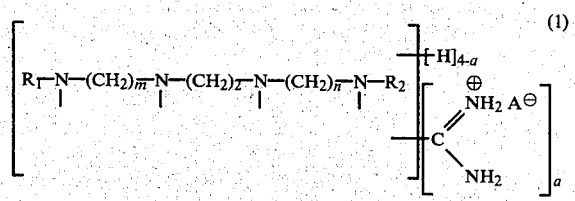

in which $R_1$ and $R_2$ are identical or different and denote alkyl, 2-hydroxyalkyl or alkenyl each having from 8 to 18 carbon atoms, or $C_8$–$C_{18}$ alkoxypropyl, m and n are 2 or 3, a is a number from 1 to 4 and A denotes an anion.

Preferred compounds of the formula 1 are those in which $R_1$, $R_2$ and a are as defined above, m and n are 3 and A denotes the acetate ion.

The compounds of the invention are prepared by reaction of 1 mol of a compound of the formula 2

$$R_1\text{-NH}-(CH_2)_m-\text{NH}-(CH_2)_2-\text{NH}-(CH_2)_n-\text{NH}-R_2 \quad (2)$$

with 1 to 4 mols of cyanamide in the presence of an acid. The reaction is preferably carried out in water or a lower alcohol at a temperature of from 40° to 100° C., preferably 50° to 90° C. It proved advantageous first to add the acid to the amine of the formula 2 in order to produce the corresponding salt. Next, the salt obtained is admixed with an aqueous or alcoholic solution of cyanamide and allowed to react for about 2 to 5 hours while stirring. Suitable acids are mineral acids, acetic acid, lactic acid, formic acid, gluconic acid, or other organic acids, preferably acetic acid.

Another possibility to prepare compounds of the formula 1 is the reaction of a compound of the formula 2 with methoxy-urea sulfate or S-methylthiourea sulfate in aqueous and/or alcoholic solution. In this case, an acid need not be added separately as it is the case with the reaction with cyanamide.

Depending on the molar proportion of the amine of formula 2 and cyanamide, methoxyurea sulfate or S-methylthiourea sulfate, up to 4 guanidinium groups can be incorporated. Since all four amino groups are equal, the exact position of the guanidinium groups cannot be determined if less than 4 mols of cyanamide, methoxyurea sulfate or S-methylthiourea sulfate are added.

The amines of the formula 2 used as starting products are obtained by the process described in German Offenlegungsschrift No. 2,938,710 by reacting alkylalkylene diamines of the formula

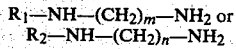

with glyoxal to give bisaldimines of the formula

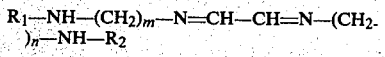

and thereupon reducing the bisaldimines catalytically.

The synthesis yields the compounds of the formula 1 according to the invention in the form of brown, more or less viscous, liquids which can be mixed with water and/or lower alcohols in any desired ratio. The pure products can be obtained as pastes by distilling off the solvent.

The compounds of the invention are distinguished by a pronounced biocidal effect on gram-positive and gram-negative bacteria, mould fungi and algae. It should be noted, in particular, that they have an outstanding effect against sulfate-reducing bacteria of the type Desulfovibrio desulfuricans, the metabolites of which, especially hydrogen sulfide, are responsible for immense corrosion damages in oil wells, oil pipelines, crude oil refineries, flooding water pipes and flooding water pressure wells. Moreover, bacteria of the aforesaid type develop a resistance very rapidly so that a frequent change of the bactericide is necessary and, hence, a wide offer of products of this type is required. The excellent solubility of the compounds of the invention makes it possible to use highly concentrated solutions, for example in alcohols, which can be further diluted with water and exactly dosed on the spot, which is of great importance for the use in oil industries.

Because of their excellent and broad range of efficiency, their good solubility in water and and skin tolerance, the compounds of the invention can be used successfully and quite generally as disinfectants. Due to their good short-term efficiency, the compounds can also be used as disinfectants for hands and surfaces.

To prepare liquid preparations of such disinfectants water or lower alcohols, for example, isopropanol, or water/alcohol mixtures are generally used. The preparations contain 5 to 70% by weight, preferably 20 to 55% by weight of the guanidinium compounds of the invention. For making the liquid preparations the solutions obtained in the synthesis of the guanidinium compounds can be used directly. The solutions are diluted to the desired final concentration by the addition of water or alcohol. The formulations may, of course, further contain other substances and auxiliaries as used in conventional formulations of this kind, for example, catianic or non ionic surface-active substances, electrolytes, complex forming agents, dissolving intermediaries, lower aldehydes, for example, formaldehyde, glyoxal or glutardialdehyde, as well as dyestuffs and perfumes. The additives are used, for example, for improving the wetting property, the stability in hard water, for adjusting the viscosity and to improve the resistance to cold of the solutions.

The following examples illustrate the invention.

EXAMPLE OF PREPARATION 1

252 g (0.4 mol) of N,N'-dilaurylaminopropyl ethylenediamine are heated to 75° C. and at that temperature 420 g (1.4 mols) of 20% acetic acid are added drop by drop. To complete the formation of the amine salt stirring of the mixture is continued for 15 minutes at 75° C. At that temperature 116 g (1.38 mols) of 50% aqueous cyanamide solution are then dropped in and stirring is continued for 4 hours. The resulting clear, reddish-brown solution has a pH of 7, which is adjusted to 6.5 by adding 50% acetic acid. Free cyanamide cannot be detected in the reaction mixture. The reaction product is a clear liquid of 45% strength.

EXAMPLE OF PREPARATION 2

54.2 g (0.085 mol) of N,N'-dialaurylaminpropyl ethylenediamine are added to 320 g of 6% acetic acid and dissolved therein while heating and with simultaneous formation of the amine salt. At 70° C., 12.6 g (0.3 mol) of cyanamide dissolved in 15 ml of water are added over a period of 20 minutes. Stirring of the mixture is continued for 5 hours at 70° C. A clear, thinly liquid solution of 23% strength is obtained having a pH of 6.4, measured as a 1% solution. Free cyanamide cannot be detected in the reaction mixture.

EXAMPLE OF PREPARATION 3

252 g (0.4 mol) of N,N'-dilaurylaminopropyl ethylenediamine and 80 g of isobutanol are heated to 70° C. and, at that temperature, 48 g (0.8 mol) of glacial acetic acid are added drop by drop over a period of 20 minutes. The mixture is stirred for a short while whereupon 282 g (0.8 mol) of 12% aqueous cyanamide solution are added at 70° to 80° C. over a period of 40 minutes. Stirring of the mixture is continued under nitrogen, for 2 hours at 70°–80° C. and then for 2 hours at 90° to 95° C. The mixture is then allowed to cool to 30° to 40° C. and 48 g of glacial acetic acid and thereafter 60 g of isopropanol are added. The reaction product is a clear liquid of 50% strength in which free cyanamide cannot be detected.

EXAMPLE OF PREPARATION 4

57.2 g (0.1 mol) of N,N'-dilaurylaminopropyl ethylenediamine are dissolved in 20 g of isobutanol with heating. At 70° C., 24 g (0.4 mol) of acetic acid are added drop by drop over a period of 25 minutes. The reaction mixture is heated to 75° to 80° C. and at that temperature 33.6 g (0.4 mol) of 50% aqueous cyanamide solution are added drop by drop over a period of 20 minutes. 45 g of water are added and stirring of the mixture is continued for 3 hours at 90° to 95° C. The clear liquid obtained has a concentration of 53% and a pH of 6.4.

The constitutions of the compounds of the formula 1 obtained according to Examples 1 to 4 are given in the table below:

| Examples 1 to 4: |
|---|
| $R_1 = R_2 =$ lauryl alcohol (75% $C_{12}$, 25% $C_{14}$) |
| $m = n = 3$ |
| $A =$ acetate |
| Example 1: $a = 3.5$ |
| Example 2: $a = 3.5$ |
| Example 3: $a = 2$ |
| Example 4: $a = 4$ |

EXAMPLE OF APPLICATION I

To test the bactericidal and fungicidal effect a suspension containing about $10^6$ germs/ml is used. The time of action is 24 and 48 hours at 20° C. In the table there are listed the minimum microbiocidal concentrations in μg/ml.

| product of Example | Staph. aur. | E. coli | Ps. aerug. | Prot. vulg. | Cand. alb. |
|---|---|---|---|---|---|
| 1: 24 hrs | 31 | 31 | 16 | 16 | 31 |
| 2: 24 hrs | 31 | 31 | 16 | 62 | 16 |
| 3: 24 hrs | 16 | <4 | 8 | <4 | 16 |
| 4: 24 hrs | 125 | 62 | 31 | 8 | 16 |
| 1: 48 hrs | 8 | <4 | 16 | 8 | 8 |
| 2: 48 hrs | <4 | <4 | 16 | 16 | 16 |
| 3: 48 hrs | <4 | <4 | <4 | <4 | <4 |
| 4: 48 hrs | 8 | <4 | 16 | <4 | 8 |
| comparative product: 24 hrs | 8 | 16 | 16 | 125 | 125 |
| comparative product: 48 hrs | <4 | 8 | 16 | 16 | 16 |

Comparative product: cocosalkyldimethylbenzylammonium chloride

EXAMPLE OF APPLICATION II

To test the bactericidal and fungicidal short term effect a suspension as specified in Example I is used, the time of action being 1 hr and 4 hours. In the table are listed the minimum microbiocidal concentrations in μg/ml.

| Product of Example | Staph. aur. | E. coli | Ps. aerug. | Prot. vulg. | Cand. alb. |
|---|---|---|---|---|---|
| 2: 1 hr | 62 | 500 | 62 | 2000 | 500 |
| 4: 1 hr | 1000 | 1000 | 125 | 1000 | 500 |
| 2: 4 hrs | 62 | 16 | 62 | 31 | 500 |
| 4: 4 hrs | 1000 | 125 | 125 | 62 | 62 |
| comparative product: 1 hr | 250 | 16 | 32 | 16 | 125 |
| comparative product: 2 hrs | 16 | 16 | 16 | 16 | 62 | comparative product: cocosalkyldiamine biguanidinium acetate

EXAMPLE OF APPLICATION III

To test the bactericial effect on Desulfovibro desulfuricans suspensions are used under the conditions of Example I. The minimum microbicidal concentration in μg/ml is indicated in the following table:

| Product of Example | Desulf. des. Nr. 39 | Desulf. des. Nr. 85 |
|---|---|---|
| 1: 24 hrs | 8 | 8 |
| 1: 48 hrs | 8 | 8 |
| 2: 24 hrs | 62 | 62 |
| 2: 48 hrs | 16 | 8 |
| 3: 24 hrs | 8 | 4 |
| 3: 48 hrs | 8 | 4 |
| 4: 24 hrs | 4 | 4 |
| 4: 48 hrs | 4 | 4 |
| Comp. 24 hrs | 64 | 64 |
| Comp. 48 hrs | 64 | 32 |

Comparative product as defined in Example I.

EXAMPLE OF APPLICATION IV

To test the effect of disinfection on surfaces with Staph. aur and Klebs. pneum. 50×50 mm samples of laminated plastic, PVC floor covering and tiles for operating theaters are inoculated with suspensions containing $10^8$ to $10^9$ germs per ml of CSL suspension. After drying of the germ suspension (90 minutes), the disinfectants are sprayed onto the surfaces from a distance of 30 to 40 cm.

Composition of the formulations:

| A: | 11.1% of the product obtained in Example 1 |
|---|---|
|  | 5% of nonylphenol 10 EO-polyglycol ether |
| balance to | 100% water |
| B: | 11.1% of the product obtained in Example 1 |
|  | 5% of nonylphenol 10 EO-polyglycol ether |
|  | 5% of formalin of 35% strength |

| formulation | 4% of glyoxal of 40% strength |
|---|---|
| | 5% of isopropanol |
| balance to | 100% water. |

| | Test results | | | | | | | |
|---|---|---|---|---|---|---|---|---|
| | residual germ content* (KBE) | | | | | | | |
| formulation | Staph. aur. | | | | Klebs. pneum. | | | |
| diluted with H₂O | 1 | 2 | 4 | 6 hrs | 1 | 2 | 4 | 6 hrs |
| A 1:10 | 0 | 0 | 0 | 0 | 100 | 50 | 50 | 50 |
| B 1:10 | 0 | 0 | 0 | 0 | 0 | 0 | 0 | 0 |
| A 1:100 | 30 | 0 | 0 | 0 | 30 | 20 | 20 | 20 |
| B 1:100 | 20 | 20 | 20 | 20 | 100 | 100 | 100 | 100 |

*in conformity with the recommendations for testing and evaluating the efficiency of chemical disinfection processes (Zbl. Bakt. Hyg. I Abt. Orig. B 165, 335-380 (1977).

What is claimed is:

1. A guanidinium compound of the formula 1

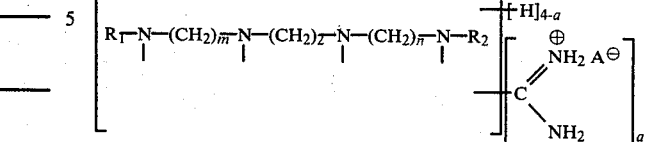

in which $R_1$ and $R_2$ are identical or different and denote alkyl, 2-hydroxyalkyl or alkenyl each having from 8 to 18 carbon atoms, or $C_8$–$C_{18}$-alkoxylpropyl, m and n are 2 or 3, a is a number from 1 to 4 and A denotes an anion.

2. Microbiocidal agent comprising a solution containing 5 to 70% percent of a guanidinium compound as claimed in claim 1 in water, lower alkanols or mixtures thereof.

* * * * *